United States Patent
Yelin et al.

(10) Patent No.: US 11,547,315 B2
(45) Date of Patent: Jan. 10, 2023

(54) BLOOD VELOCITY MEASUREMENT USING CORRELATIVE SPECTRALLY ENCODED FLOW CYTOMETRY

(71) Applicant: TECHNION RESEARCH & DEVELOPMENT FOUNDATION LIMITED, Haifa (IL)

(72) Inventors: Dvir Yelin, Haifa (IL); Tal Elhanan, Haifa (IL)

(73) Assignee: TECHNION RESEARCH & DEVELOPMENT FOUNDATION LIMITED, Haifa (IL)

(*) Notice: Subject to any disclaimer, the term of this patent is extended or adjusted under 35 U.S.C. 154(b) by 400 days.

(21) Appl. No.: 16/891,204

(22) Filed: Jun. 3, 2020

(65) Prior Publication Data

US 2020/0288992 A1 Sep. 17, 2020

Related U.S. Application Data

(63) Continuation of application No. 14/751,313, filed on Jun. 26, 2015, now abandoned.

(60) Provisional application No. 62/017,749, filed on Jun. 26, 2014.

(51) Int. Cl.
*G06V 10/00* (2022.01)
*A61B 5/026* (2006.01)
*A61B 5/00* (2006.01)

(52) U.S. Cl.
CPC ........ *A61B 5/0261* (2013.01); *A61B 5/7246* (2013.01); *A61B 2562/0238* (2013.01)

(58) Field of Classification Search
CPC .. H04N 11/146; H04N 11/165; H04N 11/186; A61B 5/0261; A61B 5/7246; A61B 5/1405; A61B 2562/0238; A61B 2576/00; G01N 15/1475; G06T 7/20
See application file for complete search history.

(56) References Cited

U.S. PATENT DOCUMENTS

| | | | |
|---|---|---|---|
| 6,258,046 B1* | 7/2001 | Kimball | A61B 8/12 600/593 |
| 7,113,817 B1* | 9/2006 | Winchester, Jr. | A61B 5/0059 600/478 |
| 9,733,460 B2 | 8/2017 | Kang et al. | |
| 9,984,277 B2* | 5/2018 | Castro-Gonzalez | G06V 10/431 |

(Continued)

OTHER PUBLICATIONS

Flow cytometry using spectrally encoded confocal microscopy L. Golan and D. Yelin, one of the present inventors, and published in Optics letters, 2010. vol. 35(13), pp. 2218-2220 (3 pages).

(Continued)

*Primary Examiner* — Amir Alavi
(74) *Attorney, Agent, or Firm* — Roach Brown McCarthy & Gruber, P.C.; Kevin D. McCarthy

(57) ABSTRACT

A spectrally encoded flow cytometry (SEFC) technique for imaging blood in the microcirculation. Since the dependency of one of the axes of the image on time prevents effective quantification of essential clinical parameters, the optical path in an SEFC system is split into two parallel imaging lines, followed by data analysis for recovering the flow speed from the multiplexed data. The data analysis may be auto-correlation of a pair of images obtained from a sequence of images of the imaged blood vessel.

16 Claims, 3 Drawing Sheets

(56) References Cited

U.S. PATENT DOCUMENTS

| | | | |
|---|---|---|---|
| 2002/0093641 A1* | 7/2002 | Ortyn | G01N 15/147 356/28 |
| 2003/0124516 A1* | 7/2003 | Chung | C12N 5/0093 435/5 |
| 2004/0127800 A1* | 7/2004 | Kimball | A61B 5/14539 600/483 |
| 2007/0087445 A1 | 4/2007 | Tearney et al. | |
| 2007/0109546 A1 | 5/2007 | Meshulach et al. | |
| 2010/0045778 A1 | 2/2010 | Yelin | |
| 2011/0137178 A1 | 6/2011 | Tearney et al. | |
| 2013/0107274 A1 | 5/2013 | Vertikov et al. | |
| 2013/0222801 A1 | 8/2013 | Harel et al. | |
| 2015/0230708 A1 | 8/2015 | Wang et al. | |
| 2015/0374246 A1* | 12/2015 | Yelin | A61B 5/0261 600/479 |
| 2018/0110462 A1* | 4/2018 | Asvadi | G01N 33/5094 |
| 2018/0203009 A1* | 7/2018 | Vittorino De Almeida | G16H 10/40 |
| 2019/0005351 A1* | 1/2019 | Zhou | G06T 7/246 |
| 2020/0288992 A1* | 9/2020 | Yelin | A61B 5/0261 |
| 2021/0321967 A1* | 10/2021 | Daerr | G01N 33/49 |

OTHER PUBLICATIONS

Rossow, "Scanning laser image correlation for measurement of flow", Journal of Biomedical Optics, 15(2) Mar./Apr. 2010 (8 pages).

Wong et al. "Otical time-stretch confocal microscopy at 1um", Optics Letters, Vo. 37, No. 16, 2012 (3 pages).

\* cited by examiner

BLOOD VELOCITY MEASUREMENT USING CORRELATIVE SPECTRALLY ENCODED FLOW CYTOMETRY

FIELD OF THE INVENTION

The present invention relates to the field of the measurement of the velocity of blood flow, especially by measurement of the flow in subcutaneous vessels by means of optical spectrally encoded analysis methods.

BACKGROUND

Quantitative information on blood composition and blood cell morphology is frequently used for patient diagnosis using flow cytometry complemented by chemical analysis and optical microscopy. In recent years, several methods for obtaining useful clinical data from small drops of extracted blood have been developed, reducing pain and anxiety to patients. Non-invasive optical techniques for measuring key clinical indices of blood have also been demonstrated and shown clinically useful, including pulse oximetry, photothermal imaging and orthogonal polarized spectral imaging. While limited by the accuracy of their data, these technologies are attractive for many applications that require real-time diagnosis, involve difficult extraction of blood, and where proper sample handling cannot be maintained.

In the article entitled "Flow cytometry using spectrally encoded confocal microscopy" by L. Golan and D. Yelin, one of the present inventors, and published in Optics letters, 2010. Vol. 35(13), pp. 2218-2220, there is described a technique termed spectrally encoded flow cytometry (SEFC), which has been shown effective for noninvasive, high-resolution imaging of blood flowing in the microcirculation. Reference is now made to FIG. 1, adapted from that article, which shows schematically the way in which SEFC is performed. A portable handheld probe is used to image the blood vessel 16 being assessed. In FIG. 1, that vessel is shown with blood cells 15 flowing therein, and it could be a small, optically accessible blood vessel, such as those in the mucous tissues. A broadband light source 10 is input by means of a focusing lens 11 into a fiber 12, and the light is spectrally dispersed by means of a diffraction grating 13 and a high NA lens 14, to form a spectrally encoded confocal line 19 on the blood vessel 16. The term spectrally encoded is used in this disclosure to include both a light beam that has information impressed on it spatially, such as by dispersing the light using a diffracting element so that it has different spectral properties, i.e. its wavelength, at different locations across the beam, or also, to include a light beam that has wavelength dependent information impressed on it, such as is present when different spatially dispersed wavelengths are reflected from the blood vessels, and the different wavelengths of light therefore carry information about the level of the reflected light. The lens 14 then images the reflectance of the spectrally encoded confocal line 19 positioned at the cross-section of the blood vessel, and the reflected light is passed back through the optical fiber 12. As cells 15 within the blood stream cross the spectrally encoded line 19, backscattered light is repeatedly recorded to form a two-dimensional confocal image of the cells, without additional mechanical scanning. When the spectrally encoded line 19 is positioned perpendicular to the direction of flow, the resulting two-dimensional SEFC data is spanned by the spectrally encoded line 19, encoding the x-(Cartesian) coordinate, while the y-coordinate is encoded by time, as indicative of the flow. This image data is collimated by a lens 17 and input into a spectrometer and control apparatus, 18, where the data is spectrally analyzed or decoded to generate a two dimensional time sequenced image of the blood flow. Using this prior art SEFC system, cells flowing at higher velocities appear shorter along the x-axis compared to slower moving cells of similar morphology, resulting in an inability to estimate their true proportions. Perhaps more importantly, obtaining key clinical parameters that involve cell counts, such as red, white, differential and platelet counts, requires knowledge of the exact imaged volume for effectively extrapolating the measured parameters to the entire body. This is self-evident since, even if the number of cells passing is counted, the volumetric concentration in the blood stream, which is what is commonly known as the "blood count", also requires knowledge of the volume in which that number of cells counted was performed, and in order to determine that volume, the flow rate of the blood must be determined. Thus, transforming the time axis into a physical 'y' axis requires precise, real-time measurement of the blood flow velocity across the field of view. Although non-invasive flow velocity measurements in the microcirculation had been previously demonstrated using laser speckle contrast analysis, laser Doppler and orthogonal polarized spectral imaging, these techniques provide only averaged measurements and would be difficult to integrate into an SEFC system.

There therefore exists a need for a method of measuring blood flow velocity in an SEFC system, which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems and methods, utilizing a correlative SEFC technique, for measuring flow velocities in the microcirculation in real-time and at high spatial accuracy. Blood flow velocities in small mesentery vessels are estimated by spatially spectrally encoded an imaging beam, such as by dispersion through a diffraction grating, and splitting the dispersed beam into separate paths, which are then focused in the form of spectrally encoded lines onto two closely positioned locations across the flow path of the blood stream in the measurement region. By measuring temporal correlations of the flow patterns obtained from the light patterns reflected from the two line locations along the vessel, accurate velocity measurement of the imaged cells can be made. An advantage of this correlative SEFC method for measuring blood velocity is that it relies on high-resolution confocal images that allow effective extraction of microscopic flow.

The input beam can be split by any method which allows the two separated beams to be accurately focused on positions very close to each other. One method is by using a beam splitter to laterally divert part of the incident beam, and a diverting mirror to deflect the laterally split-off beam back towards the direction of the original incident beam, but from a slightly offset location. The angle of the diverting mirror can be such as to cause the two split beams to focus onto the blood vessel in very closely located positions. An alternative method is to use a wedge for angularly diverting part of the input beam, such that the two beams—the diverted and the undiverted beam—are confocally focused across the blood flow as lines in close longitudinal positions. The wedge may be positioned such that it diverts only part of the beam, thus generating the double beam—one from the raw incident beam, and the other from the wedge refracted section of the beam.

The spectrally encoded and spatially dispersed beams returned from the blood vessel can be recombined spatially to facilitate transmission back from the probe to the analysis unit, and then analyzed spectrally to extract the lateral features of the blood flow image. Autocorrelation between twin images of blood cells obtained from the two reflected beams enables the time lag between the two images from each beam to be determined, from which the blood cell velocity can be calculated.

There is thus provided in accordance with an exemplary implementation of the methods described in this disclosure, a method for velocity measurement of cells in a vessel, comprising:
(i) directing a broadband illuminating beam towards the vessel,
(ii) spectrally dispersing the beam in a direction across the direction of flow of the cells in the vessel,
(iii) splitting the beam, in a direction generally perpendicular to the direction of the spectral dispersion of the beams, into two beams,
(iv) focusing each of the beams into a separate line of illumination on the vessel, the lines being aligned generally across the vessel,
(v) collecting light reflected from the vessel along the illumination lines,
(vi) spectrally decoding the reflected light to generate a sequence of two dimensional images of the motion of the cells along the vessel, and
(vii) performing signal processing on doubled images of at least one of the cells, to determine the time of passage of the at least one cell between the two lines.

In the above described method, the signal processing may involve auto-correlation performed on the images. Additionally, the spectral dispersing may be performed by using a diffraction grating.

In other implementations of this method, the lines may be sufficiently closely disposed to each other, that the transit time of the cells between the lines facilitates the measurement of the velocity of the cells. In some implementations, these closely disposed lines may be separated by no more than a distance of 100 microns.

Furthermore, in these methods, the splitting of the beam may performed by disposing a wedge in part of the beam. In such a case, the wedge should be orientated such that it deflects that part of the beam which passes through it in a direction essentially perpendicular to that of the spectral dispersion. Alternatively, the splitting of the beam may be performed by disposing a beam splitter and laterally disposed reflector in the path of the beam.

Further example implementations involve a system for velocity measurement of cells in a vessel, comprising:
(i) a broadband source directing an illuminating beam towards the vessel,
(ii) an element for spectrally dispersing the beam in a direction across the direction of flow of the cells in the vessel,
(iii) a beam splitting unit disposed to split the beam in a direction generally perpendicular to the direction of the spectral dispersion of the beams, into two beams,
(iv) a focusing lens positioned to focus each of the beams into a separate line of illumination on the vessel, the lines being aligned generally across the vessel,
(v) a spectral analyzer for receiving spectrally encoded beams reflected from the vessel along the two illumination lines, to generate a sequence of two dimensional images of the motion of the cells along the vessel, and
(vi) a signal processor adapted to analyze doubled images of at least one of the cells, to determine the time of passage of the at least one cell between the two lines.

In the above described system, the signal processor may include an auto-correlator for determining the time lag of the features in the images. Additionally, the element for spectrally dispersing the beam may be a diffraction grating.

In other implementations of this system, the lines should be sufficiently closely disposed to each other, that the transit time of the cells between the lines facilitates the measurement of the velocity of the cells. In some implementations, these closely disposed lines may be separated by no more than a distance of 100 microns.

Furthermore, in these systems, the beam splitting unit may be a wedge disposed in part of the beam. In such a case, the wedge should be orientated such that it deflects the beams passing through it in a direction generally perpendicular to that of the spectral dispersion. Alternatively, the beam splitting unit may be a combination of a beam splitter and a laterally disposed reflector.

BRIEF DESCRIPTION OF THE DRAWINGS

The present invention will be understood and appreciated more fully from the following detailed description, taken in conjunction with the drawings in which.

DETAILED DESCRIPTION

Figure 1:
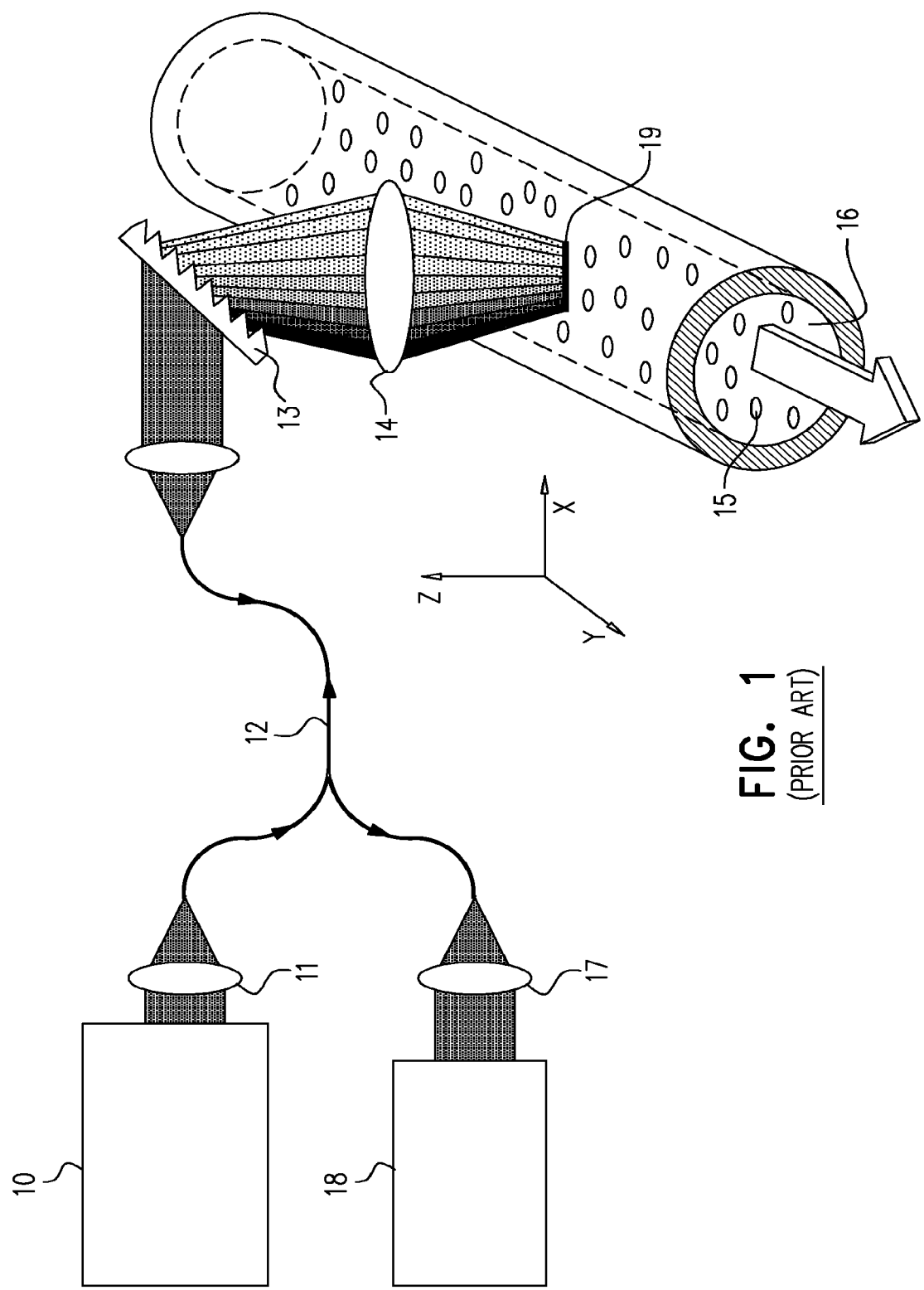
FIG. 1 shows a prior art spectrally encoded flow cytometry (SEFC) system, used for obtaining a two dimensional image of the passage of blood cells down a vessel.
Figure 2:
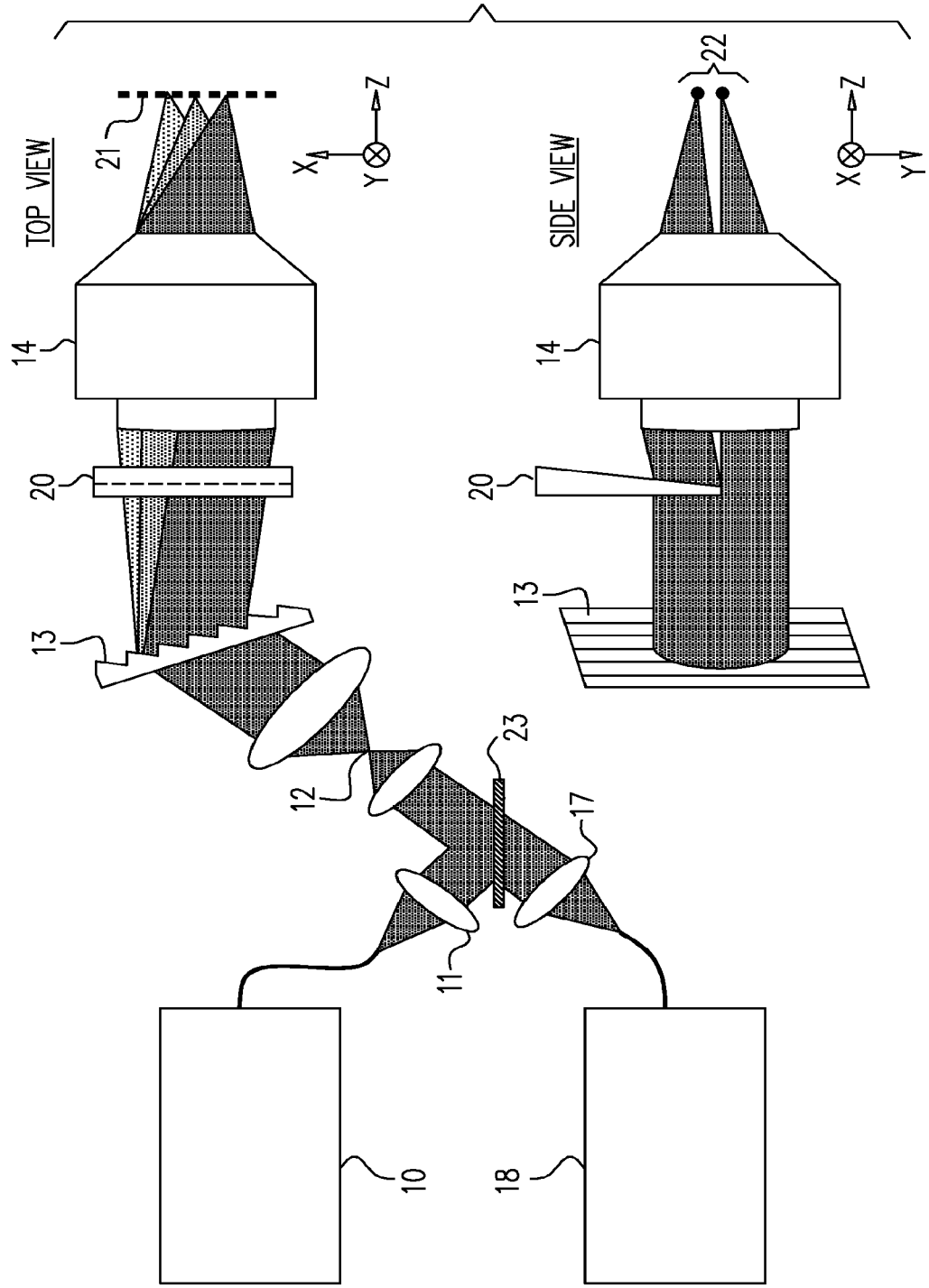
FIG. 2 illustrates schematically a system for the measurement of blood velocity when imaging capillary blood flow in patients using spectrally encoded double beams.

Reference is now made to FIG. 2, which illustrates schematically an exemplary system for the measurement of blood velocity when imaging capillary blood flow in patients using spectrally encoded double line beams. The system of FIG. 2 uses a wedge in order to generate the two incident mutually offset line beams. Broadband light from a source 10 such as fiber-coupled superluminescent diode array is collimated by the lens 11, and, as in FIG. 1, may be transmitted to the measurement probe through a fiber 12 (not shown). It is then dispersed in the y-axis using a transmission diffraction grating 13, having 1200 lines/mm in the exemplary system described herein. The dispersed beam is then split in the direction of the x-axis, as shown in the drawing labelled "SIDE VIEW", using a 0.5° wedge prism inserted essentially halfway into the beam cross section, such that half of the beam continues undiverted, and the other half is diverted by the wedge angle. The two split halves of the beam are then focused into two approximately equal-intensity transverse focused illumination lines using, in the example system of FIG. 2, a water-immersion objective lens having a numerical aperture (NA)=1.2, and a magnification of ×60.

Looking at the focal plane of the incident light, it is seen from the drawing marked "TOP VIEW" that the focused light of each split section of the beam is spectrally dispersed along the x-axis direction, as shown by the points 21 that are representatives of illumination lines on a vessel. The spatial splitting of the beam into the two adjacent focused line beams, on the other hand is performed along the y-axis direction, as shown by the two focal points 22—that are representatives of illumination lines on a vessel—on the SIDE VIEW part of the drawing. As is observed, the blood vessel is oriented along the y-axis direction, such that the spectrally encoded light spread along the x-axis direction is across the flow direction of the blood stream to be measured, while the two spectrally encoded focused line beams are separated in the y-direction along the axis of the blood vessel.

At the focal plane, the y-axis separation between the spectrally encoded lines, namely the on-axis and the off-axis spatially diverted lines, is of the order of 24 µm in the example system shown in FIG. 2, and was measured in that system by translating a sharp edge along the y-axis in the image plane. Backscattered light from the blood vessel and its overlying tissue is collected by the objective lens 14, returned to the instrument control module and may be directed by a beam splitter 23 into a single-mode fiber which inputs it for decoding analysis by a high-speed spectrometer incorporated within the analysis and control module 18. The spectrometer typically includes a collimating lens, a transmission diffraction grating and a line-CCD camera for generating the spectrally analyzed images. This system thus differs from the prior art SEFC system shown in FIG. 1 by incorporation of the beam splitting element, in this exemplary implementation, a wedge prism. Without the prism, the spectrometer records the reflections along a single spectrally encoded line, forming an image of the cells flowing across it. With the wedge prism inserted into the beam, reflections from both lines are combined on the spectrometer camera, forming a line-image that is the coherent summation of the reflections from both spectrally encoded lines. The temporal separation between the pairs of lines is used in order to calculate the blood velocity, and the simplest method of determining this separation is by performing autocorrelation analysis of the pairs of images in the sequence of frames.

The images may be acquired and then processed using any sort of image processing software, such as the MatLab® program. A two dimensional autocorrelation can be performed on the resulting image using an autocorrelator, which is incorporated together with the signal processor within the analysis and control module 18. Each detected element in the flow essentially appears twice in the raw images—first by reflecting light from the first spectrally encoded line, and again when that element passes the second focused line. The acquired images thus incorporate information on the time it took a single element to pass the distance between the two spectral lines. In the autocorrelation procedure, this time shift is equivalent to the distance between the first autocorrelation peak to the center peak along the y-axis. The flow velocity v may be calculated using $v=L/\tau$, where L denotes the separation between the spectrally encoded lines and $\tau$ denotes the measured time-delay coordinate of the first autocorrelation peak.

Figure 3:
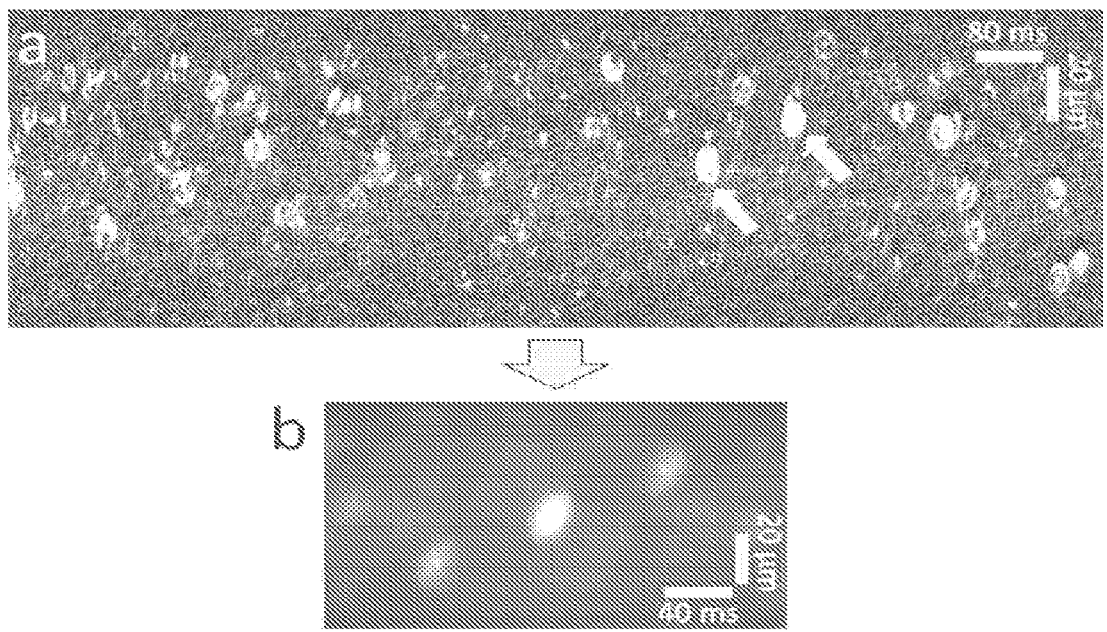
FIG. 3 shows images which illustrate the results of an actual measurement on a blood flow performed using the system described in FIG. 2.

Reference is now made to FIG. 3, which shows in the top image marked "a", the results of an actual measurement performed using the system described in FIG. 2, on blood from a venipuncture of a healthy donor, diluted (1:5) with PBS and was pumped through an experimental flow chamber. Due to the high forward scattering of the red blood cells that rapidly reduced image quality with depth, imaging was performed at a depth of no more than approximately 10 µm within the flow itself. Numerous red blood cells are clearly visible in the raw image, most, as indicated by the arrows in the image, appeared twice with consistent shifts in the time (y) axis and small constant shifts in the wavelength-encoded x-axis. Some cells appear only once, most likely due to a component of the flow vector in the depth dimension (z-axis), causing them to disappear from (or to appear within) the focal depth of the imaging lens in the distance travelled between the two spectrally encoded illumination lines.

The two images of each particle—where a pair are imaged—are also shifted in the x-axis direction, most likely due to a small shift between the wavelength-encoded lines caused by a slight misalignment of the wedge prism, or because of the lines not being perfectly perpendicular to the direction of flow.

The lower image of FIG. 3, marked "b", shows the output image of a two-dimensional autocorrelation of the raw data of the images of FIG. 3a. As can be calculated from the first autocorrelation peak, averaged blood velocity measured in this example of a measurement, was approximately 0.45 mm/s with an estimated error (peak width) of ±0.13 mm/s.

The main advantage of correlative SEFC in measuring blood velocity is that it relies on high-resolution confocal images that allow effective extraction of microscopic flow. When desired, during an SEFC imaging session, the operator may insert the wedge prism for measuring the flow velocity for a few seconds, and then remove it for continuing high-resolution imaging using conventional SEFC.

The maximal flow velocity, $v_{max}$, that could be measured using correlative SEFC is given by:

$$v_{max} = \frac{fd}{N_{cell}}$$

where f denotes the camera line rate, d the average cell diameter and $N_{cell}$ denotes the number of pixels sampling each blood cell ($N_{cell}>2$). Using typical values of f=5 kHz, d=7 µm and $N_{cell}=3$ a maximum velocity of 11.7 mm/s is obtained, considerably higher than the typical velocities in venules and in small arterioles. The efficiency of correlative SEFC in measuring velocities also depends on the exact distance between the spectrally encoded lines—short separations are preferable for reducing the effect of the axial component of the flow, while line separation must exceed cell size for separating between the autocorrelation peaks.

When using a wedge in order to generate the beam splitting, the insertion of the wedge prism into the optical path changes the original circular beam aperture into two smaller, slightly distorted D-shaped apertures. This results in approximately 2-fold loss of resolution in the y-axis, while the x (wavelength) axis should remain largely unaffected. Common resolution measurements using reflective targets are not feasible at this configuration due to inherent coupling between the two beams, which prevent specular reflections from being collected by the fiber aperture.

Figure 4:
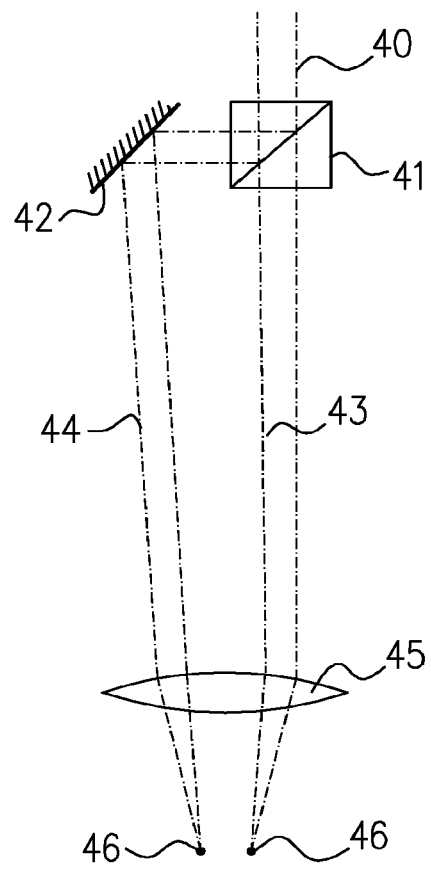
FIG. 4 illustrates an alternative method of implementing the double line focused illumination requirement of the present systems, using conventional beam-splitters and mirrors.

Reference is now made to FIG. 4, which illustrates an alternative method of implementing the double line focused illumination requirement of the present methods, using conventional beam-splitters and mirrors. The illumination beam 40 impinges on a miniature cubic beam splitter 41, such that one part 43 of the beam is transmitted towards the target region undeflected, whilst the other part is directed to a plane mirror 42, angled so that its reflected beam 44 is directed towards the target region in a small converging angle to that of the undeflected beam 43. A focusing lens 45 is used to focus both the undeflected beam 43 and the deflected beam 44 onto the two respective focal lines 46 on the blood vessel to be assessed. Despite some signal loss and added complexity, this implementation maintains the full apertures of both beams and, by allowing sufficient optical path difference between the beams, prevents undesired interference effects. Finally, correlative SEFC could be used as a standalone technique for measuring blood flow velocities in the microcirculation with high accuracy.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method for velocity measurement of cells in a vessel, comprising:
    directing a broadband illuminating beam towards said vessel;
    spectrally dispersing said beam in a direction across the direction of flow of said cells in said vessel;
    splitting said beam, in a direction generally perpendicular to the direction of the spectral dispersion of said beams, into two beams;
    focusing each of said beams into a separate line of illumination on said vessel, said lines being aligned generally across said vessel;
    collecting light reflected from said vessel along said illumination lines;
    spectrally decoding said reflected light to generate a sequence of two dimensional images of the motion of said cells along said vessel; and
    performing signal processing on doubled images of at least one of said cells, to determine the time of passage of said at least one cell between said two lines.

2. A method according to claim 1 wherein said signal processing involves auto-correlation performed on said images.

3. A method according to claim 1, wherein said spectral dispersing is performed by using a diffraction grating.

4. A method according to claim 1 wherein said lines are sufficiently closely disposed to each other, that the transit time of said cells between said lines facilitates the measurement of said velocity of said cells.

5. A method according to claim 4 wherein said closely disposed lines are separated by no more than a distance of 100 microns.

6. A method according to claim 1 wherein said splitting of said beam is performed by disposing a wedge in part of said beam.

7. A method according to claim 6 wherein said wedge is orientated such that it deflects the beams passing through it in a direction generally perpendicular to that of said spectral dispersion.

8. A method according to claim 1 wherein said splitting of said beam is performed by disposing a beam splitter and laterally disposed reflector in the path of said beam.

9. A system for velocity measurement of cells in a vessel, comprising:
    a broadband source directing an illuminating beam towards said vessel;
    an element for spectrally dispersing said beam in a direction across the direction of flow of said cells in said vessel;
    a beam splitting unit disposed to split said beam in a direction generally perpendicular to the direction of the spectral dispersion of said beams, into two beams;
    a focusing lens positioned to focus each of said beams into a separate line of illumination on said vessel, said lines being aligned generally across said vessel;
    a spectral analyzer for receiving spectrally encoded beams reflected from said vessel along said two illumination lines, to generate a sequence of two dimensional images of the motion of said cells along said vessel; and
    a signal processor adapted to analyze doubled images of at least one of said cells, to determine the time of passage of said at least one cell between said two lines.

10. A system according to claim 9 wherein said signal processor includes an auto-correlator for determining the time lag of said features in said images.

11. A system according to claim 9, wherein said element for spectrally dispersing said beam is a diffraction grating.

12. A system according to claim 9 wherein said lines are sufficiently closely disposed to each other, that the transit time of said cells between said lines facilitates the measurement of said velocity of said cells.

13. A system according to claim 12 wherein said closely disposed lines are separated by no more than a distance of 100 microns.

14. A system according to claim 9 wherein said beam splitting unit is a wedge disposed in part of said beam.

15. A system according to claim 14 wherein said wedge is orientated such that it deflects the beams passing through it in a direction generally perpendicular to that of said spectral dispersion.

16. A system according to claim 9 wherein said beam splitting unit is a combination of a beam splitter and a laterally disposed reflector.

* * * * *